(12) United States Patent
Sammartino

(10) Patent No.: US 12,102,433 B2
(45) Date of Patent: Oct. 1, 2024

(54) FLUID COLLECTION DEVICE

(71) Applicant: LHM Innovations Pty Ltd, Warrandyte (AU)

(72) Inventor: Luke P. Sammartino, Warrandyte (AU)

(73) Assignee: LHM INNOVATIONS PTY LTD, Warrandyte (AU)

( * ) Notice: Subject to any disclaimer, the term of this patent is extended or adjusted under 35 U.S.C. 154(b) by 923 days.

(21) Appl. No.: 16/971,829

(22) PCT Filed: Dec. 4, 2018

(86) PCT No.: PCT/AU2018/051294
§ 371 (c)(1),
(2) Date: Aug. 21, 2020

(87) PCT Pub. No.: WO2019/161429
PCT Pub. Date: Aug. 29, 2019

(65) Prior Publication Data
US 2020/0390378 A1    Dec. 17, 2020

(30) Foreign Application Priority Data

Feb. 21, 2018 (AU) .............................. 2018900543

(51) Int. Cl.
*A61B 5/155* (2006.01)
*A61B 5/15* (2006.01)
*A61B 5/153* (2006.01)

(52) U.S. Cl.
CPC ........ *A61B 5/155* (2013.01); *A61B 5/150213* (2013.01); *A61B 5/150267* (2013.01); *A61B 5/150946* (2013.01); *A61B 5/153* (2013.01)

(58) Field of Classification Search
CPC .......... A61B 5/15003; A61B 5/150213; A61B 5/150251; A61B 5/150259;
(Continued)

(56) References Cited

U.S. PATENT DOCUMENTS 3,848,581 A * 11/1974 Cinqualbre ........ A61B 5/15003
600/575
4,676,256 A * 6/1987 Golden ............ A61B 5/150732
604/249

(Continued)

OTHER PUBLICATIONS

European Search Report dated Oct. 28, 2021 for European Application No. 18907287.9-1132.

*Primary Examiner* — Benjamin S Melhus
*Assistant Examiner* — Severo Antonio P Lopez
(74) *Attorney, Agent, or Firm* — Greer, Burns & Crain, Ltd.

(57) ABSTRACT

The present disclosure provides a fluid collection device, including: a body having an axial bore with a fluid inlet at one end of the bore, the fluid inlet configured to connect directly or indirectly to a needle adapted to penetrate a subject to sample fluid; and two or more integrally formed fittings projecting from the body, the fittings each having an outlet in fluid communication with the inlet; each fitting configured to directly releasably couple to a collection tube such that fluid collected by the needle flows through the inlet, through the body and into each of the fittings to simultaneously or successively fill the coupled collection tubes with fluid.

14 Claims, 6 Drawing Sheets

(58) Field of Classification Search
CPC ........ A61B 5/150267; A61B 5/150389; A61B 5/150946; A61B 5/153; A61B 5/154; A61B 5/1545; A61B 5/155
See application file for complete search history.

(56) References Cited

U.S. PATENT DOCUMENTS

| | | | |
|---|---|---|---|
| 5,505,721 A | 4/1996 | Leach et al. | |
| 9,677,975 B2 * | 6/2017 | Zhang | C12M 37/02 |
| 2004/0127816 A1 | 7/2004 | Galvao | |
| 2014/0155782 A1 * | 6/2014 | Bullington | A61B 10/0045 |
| | | | 600/575 |
| 2017/0156653 A1 | 6/2017 | Scott | |

* cited by examiner

FLUID COLLECTION DEVICE

CROSS-REFERENCE TO RELATED APPLICATIONS

This application is the U.S. National phase application corresponding to PCT/AU2018/051294 which was assigned an international filing date of Dec. 4, 2018 and associated with publication WO 2019/161429A1 and which claims priority to Australian Application No. 2018900543, filed Feb. 21, 2018, the disclosures of which are expressly incorporated herein by reference.

FIELD OF THE INVENTION

The present invention relates to a device and method for sampling fluid from a subject, and more particularly to the collection of multiple separate samples from a single needle insertion site.

BACKGROUND OF THE INVENTION

Techniques are known which enable fluid sampling from subjects, including venepuncture, which provides intravenous access for blood sampling from veins. The traditional method for blood collection is the syringe and needle technique, which involves inserting the needle into a vein, observing "flash-back" of blood to indicate correct positioning of the needle into a vein, and drawing up the syringe plunger to collect blood. This is an open system, whereby the blood is then transferred to collection tubes. Open systems are less than optimal due to the chance of spillage and contamination.

Closed systems are preferred, as the blood is collected directly into the collection tubes. The "vacutainer" system or vacuum extraction system has been developed as a method to sample blood intravenously. This method uses a needle attached to a tube holder, with a vacuum pressurised collection tube, called a vacutainer. A specific volume of gas is removed from the sealed tube. When the tube closure is pierced, the tube's vacuum automatically pulls in the required volume of blood. Once the tube is filled, a subsequent tube can be attached to the tube holder for filling, enabling multiple samples to be taken from a single needle insertion.

However, there are particular subsets of patients for which the syringe and needle technique consistently achieves poor results, or is not possible. One subset includes neonates, infants and children with small veins for whom there is increased difficulty in correctly positioning the needle into a vein due to movement of the patient. Another subset includes elderly, oncology, burns or obese patients with small or fragile veins, which may collapse under the amount of suction applied by a syringe or vacuum.

A technique for blood sampling for neonates, infants and children, involves syringes with a butterfly needle. Butterfly needles are much smaller than the usual needle size and are connected to the syringe via a section of thin flexible tubing. The syringe with a butterfly needle is less painful to insert into the veins and reduces the risk of vessel collapse for neonates, infants and children with small or fragile veins. The thin flexible tube allows for more patient movement during use. Butterfly needles can also be used with a vacutainer. Unfortunately, there are few techniques which are suitable for fragile adults including elderly, oncology, burns or obese patients, where the vacuum pressure can cause veins to collapse.

A further, rarely used, technique is the broken-needle technique. This requires breaking off the hub of a needle, inserting the "broken" needle into a vein, observing flash-back of the blood and allowing the blood to drip into a collection tube. The blood is sampled without suction, however this technique is dangerous as the broken-needle can slip up into the vessel, travel through the circulation and damage organs or tissues in the body.

As discussed above, there are a number of different techniques for obtaining fluid samples from a subject. Each of the techniques collects the fluid sample using different means to get the fluid to a collection tube. However, in all of the above systems, the blood sample either needs to be transferred in open systems, or only a single tube can be filled at a time. This requires removing the filled tube and successively replacing with evacuated tubes. This procedure is time consuming and also increases the risk of blood leaking during removal and replacement. When attempting to reduce suction, the speed of collection also reduces, so there is a need to provide a faster overall system.

It is therefore an object of the present invention to provide an alternative fluid collection device that overcomes one or more of the above problems, or at least provides a useful alternative.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

Accordingly, in a first aspect, the present invention provides a fluid collection device, including:
- a body having an axial bore with a fluid inlet at one end of the bore, the fluid inlet configured to connect directly or indirectly to a needle adapted to penetrate a subject to sample fluid; and
- two or more integrally formed fittings projecting from the body, the fittings each having an outlet in fluid communication with the inlet;
- each fitting configured to directly releasably couple to a collection tube such that fluid collected by the needle flows through the inlet, through the body and into each of the fittings to simultaneously or successively fill the coupled collection tubes with fluid.

In a preferred embodiment, each fitting includes a formation or aperture to create an air gap when the collection tubes are coupled, whereby the collection tubes are in fluid communication with the ambient environment to permit fluid to be passively collected into the collection tubes by forcing air out through the air gap.

In one preferred form, the fittings are generally tubular sections. An air gap may be provided by a depressed channel running along the exterior length of the fitting. When the fitting is inserted into a collection tube, the entire opening of the collection tube is not entirely occluded.

In an alternative embodiment, air gaps may be omitted and the device can be used with vacuum tubes by incorporating a piercing device into the fittings.

A filter may be positioned within each of the fittings. The filter may function to prevent back-flow of fluid once collected in the collection tube. Alternatively, or additionally, the filter may function to remove impurities in the sampled fluid before it enters the collection tube. The filter may be in the form of a cylindrical body, or a cylindrical body with an axial bore, and may be made from cellulose for example, however a person skilled in the art will appreciate alternative filter options may be utilised. The filters may be adjustably positioned by a user with respect to the respective collection tubes so as to provide targeted filling, i.e. filling of a certain volume of fluid in the collection tubes. For example, in some applications, such as when filling a coagulation tube, an exact volume of fluid is required to be collected, and the coagulation tube cannot be over-filled or under-filled.

The fittings may be shaped to accommodate connection to collection tubes having openings of a variety of diameters. For example, the outside of the fitting may include a stepped profile, such that the collection tube is pushed onto the fitting until frictionally engaged to hold in place.

The fluid inlet of the body may also be shaped to accommodate connection to needle fittings or capillary tubes of different gauges. For example, the inlet may be tapered, such that a flexible capillary tube connected to a butterfly needle could be pushed onto the end of the inlet until frictionally engaged.

The fittings may project in parallel from the same side of the body, allowing the collection tubes to be held upright in a frame. Alternatively, fittings may project from opposite sides of the body. Either of these allows the body to be placed on a flat surface and the collection tubes lay on the flat surface.

The device is preferably transparent or semi-transparent to allow for the tracking of blood through the system. The body also preferably includes a transparent portion shaped to form a lens that magnifies viewing of fluid flash-back into the body. Observation of fluid flash-back is useful for confirming good location of the needle.

Internal surfaces of the body may be configured to provide efficient movement of fluid therealong by, for example, having a low coefficient of friction. In one form, the internal surfaces of the body may be siliconized to achieve the low coefficient of friction. Alternatively or additionally, the internal surfaces may be grooved in a manner that allows for relatively faster flow of fluid therealong when compared to non-grooved surfaces.

According to a second aspect, the present invention provides a fluid collection device, including:
  a body having an axial bore with a fluid inlet at one end of the bore, the fluid inlet configured to connect directly or indirectly to a needle adapted to penetrate a subject to sample fluid;
  an integrally formed fitting projecting from the body, the fitting having an outlet in fluid communication with the inlet, wherein the fitting is configured to directly releasably couple to a collection tube such that fluid collected by the needle flows through the inlet, through the body and into the fitting to fill the coupled collection tube with fluid; and
  an end plug removably connected within the bore at an end opposite the fluid inlet, wherein the end plug is removable so as to allow a second fluid collection device to be releasably connected within the bore, wherein fluid collected by the needle may also flow through the body into the second fluid collection device to be collected.

The end plug is preferably configured to prevent loss of fluid from the fluid connection device through the bore.

Preferably, the fluid collection device is a first fluid collection device, and the second fluid collection device is of the same construction as the first fluid collection device. Accordingly, when the second fluid collection device is releasably connected within the bore of the first fluid collection device, fluid sampled by the needle preferably flows through the body of the first fluid collection device, into the body of the second fluid collection device, and then into the fitting of the second fluid collection device to fill a collection tube coupled thereto. The collection tubes coupled to the first and second fluid collection devices may be simultaneously or successively filled with fluid sampled from the needle.

Advantageously, the end plug connected within the bore of the second fluid collection device may also be removed so as to allow a third fluid collection device to be connected to the second fluid collection device, wherein the third fluid collection device is configured to also collect fluid sampled by the needle connected to the first fluid collection device. Accordingly, a plurality of the fluid collection devices may be releasably coupled together, in series, to create a fluid collection system to collect fluid sampled by the needle.

The fluid collection device according to the second aspect of the invention may include any one or more of the features described above in relation to the fluid collection device according to the first aspect of the invention.

According to a third aspect, the present invention provides a fluid collection system, including:
  at least two fluid collection devices according to the second aspect of the invention releasably coupled together, wherein the fluid collection devices are releasably coupled together by removing the end plug from at least a first one of the fluid collection devices and inserting the fluid inlet of a second one of the fluid collection devices into an opening created by the removal of the end plug from the first one of the fluid collection devices.

When at least two fluid collection devices are releasably coupled together, the distal most fluid connection device from the needle preferably includes the end plug connected thereto, such that no fluid escapes the fluid collection system during collection.

According to a fourth aspect, the present invention provides a kit, including:
  a fluid collection device, including a body having an axial bore with a fluid inlet at one end of the bore; two or more fittings projecting from the body, the fittings each having an outlet in fluid communication with the inlet;
  a needle adapted to penetrate a subject to sample fluid, the fluid inlet of the fluid collection device configured to connect directly or indirectly to the needle; and
  two or more collection tubes, whereby each fitting is configured to directly releasably couple to a collection tube such that fluid collected by the needle flows through the inlet, through the body and into each of the fittings to simultaneously or successively fill the coupled collection tubes with fluid.

The kit may include collection tubes having different volume capacities. The collection tubes may also have different diameter openings for coupling to the fitting.

The fluid collection device may be a fluid collection device according to the first aspect of the invention.

According to a fifth aspect, the present invention provides a kit, including:
  a fluid collection device, including a body having an axial bore with a fluid inlet at one end of the bore; a fitting projecting from the body, the fitting having an outlet in fluid communication with the inlet; and an end plug removably connected within the bore at an end opposite the fluid inlet;

a needle adapted to penetrate a subject to sample fluid, the fluid inlet of the fluid collection device configured to connect directly or indirectly to the needle; and a collection tube, whereby the fitting is configured to directly releasably couple to a collection tube such that fluid collected by the needle flows through the inlet, through the body and into the fitting to fill the coupled collection tube with fluid;

wherein the end plug is removable so as to allow a second fluid collection device to be connected within the bore, wherein fluid collected by the needle may also flow through the body into the second fluid collection device to be collected.

Preferably, the fluid collection device is a first fluid collection device, and the second fluid collection device is of the same construction as the first fluid collection device.

Preferably, the kit includes a plurality of the fluid collection devices and a plurality of collection tubes. A fitting of each of the plurality of fluid collection devices is preferably configured to directly releasably couple to a respective one of the collection tubes.

The fluid collection devices may be fluid collection devices according to the second aspect of the invention.

BRIEF DESCRIPTION OF THE DRAWINGS

Further aspects of the present invention and further embodiments of the aspects described in the preceding paragraphs will become apparent from the following description, given by way of example and with reference to the accompanying drawings, in which.

DETAILED DESCRIPTION OF THE EMBODIMENTS

Figure 1:
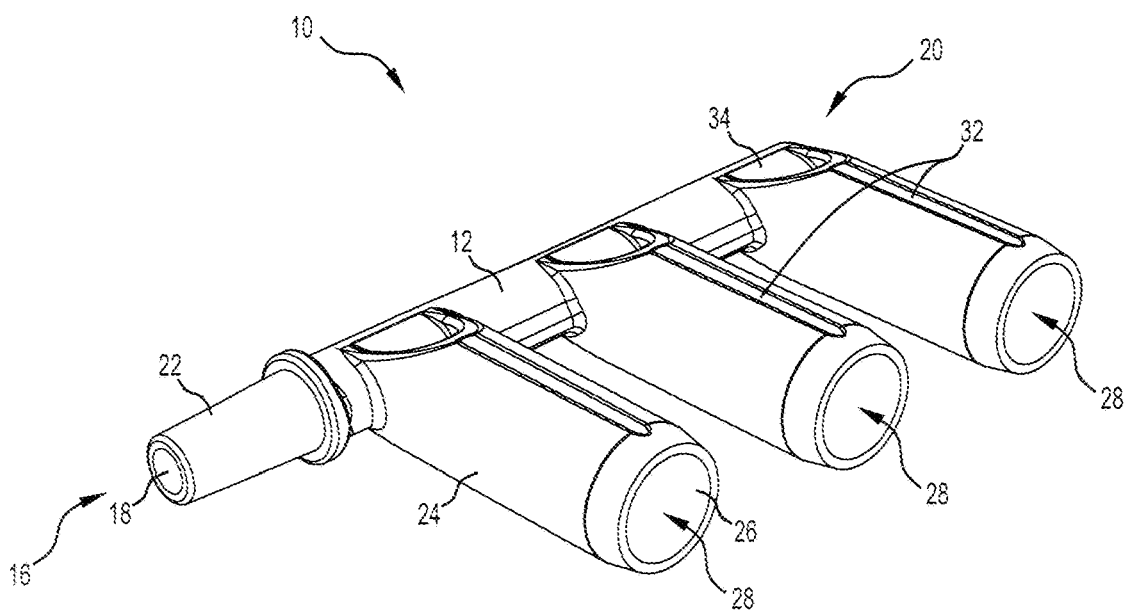
FIG. 1 shows a rear perspective view of a fluid collection device according to a first embodiment of the invention.

FIG. 1 illustrates a fluid collection device that has utility in venous blood sampling, particularly from subjects with small and/or fragile veins. Blood sampling is prevalent in general health practice, and pathology testing of sampled blood can provide important information e.g. indication of a disease state, cell counts and antibody reactions to name a few.

The fluid collection device 10 is used as a coupling and distribution device between a single needle and one or more collection tubes. The purpose of the device is to simultaneously or sequentially fill collection tubes from a single needle insertion, without having to connect or disconnect tubes during the sampling process whilst the blood is being drawn and the needle is still inserted.

Figure 3:
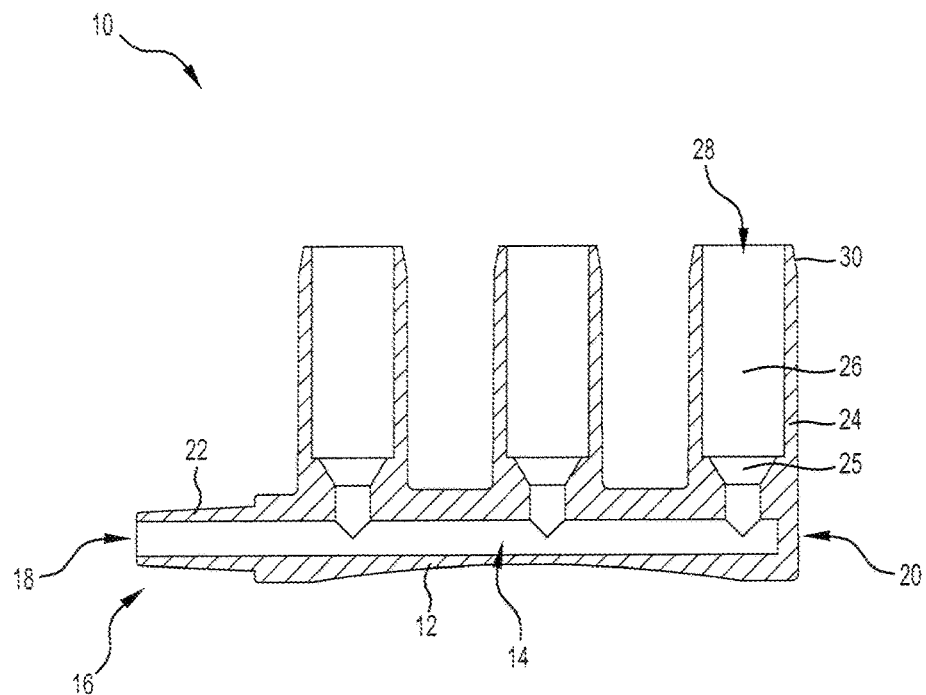
FIG. 3 shows a cross-sectional view through the fluid collection device of FIG. 2.

The device 10 has a generally elongate body 12 with an internal axial bore 14 (visible in FIG. 3). The body 12 has a first end 16 with a fluid inlet 18. The opposite second end 20 of the bore is closed.

The first end 16 includes a connection piece 22 configured to connect directly to a needle hub or indirectly to a needle hub via a flexible capillary tube (described further below).

Multiple fittings 24 project from a first side of the body 12 in a direction perpendicular to the longitudinal direction that the body 12 extends in. The fittings 24 are generally tubular sections each having a bore 26 with an outlet 28. Each outlet 28 is in fluid communication with the inlet 18. As shown in FIG. 3 the transition from the axial wall 14 to the fitting bore 26 includes a conical transition section 25 that expands the internal diameter of the flow path from the smaller axial bore 14 to the wider fitting bore 26. This difference in diameter assists in drawing the fluid towards the outlets 28 and into the collection tubes.

Figure 4:
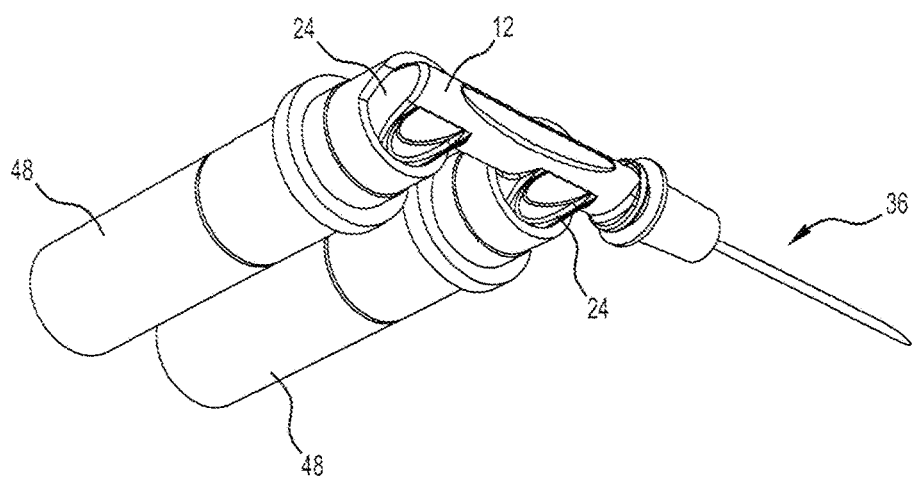
FIG. 4 shows a front perspective view of a fluid collection system and device according to a second embodiment.

The device 10 may be designed to include any number of fittings 24, where the length of the body can be longer or shorter than that shown to accommodate more or fewer spaced apart fittings. See FIG. 4, where an alternative embodiment is shown, which includes two fittings. Alternatively two or more opposing fittings may extend from the opposite side of the body to the fittings shown in FIG. 1. No matter the number of fittings, each of the outlets is in fluid communication with the inlet 18.

The device is preferably made via injection moulding, for example, so that the fittings are integrally moulded with the body. A person skilled in the art will appreciate alternative manufacturing techniques to create an integrally formed device. The device may be manufactured from plastic and is preferably transparent so that fluid flash-back is visible in the body to the user during insertion of the needle. This indicates correct needle positioning.

Figure 2:
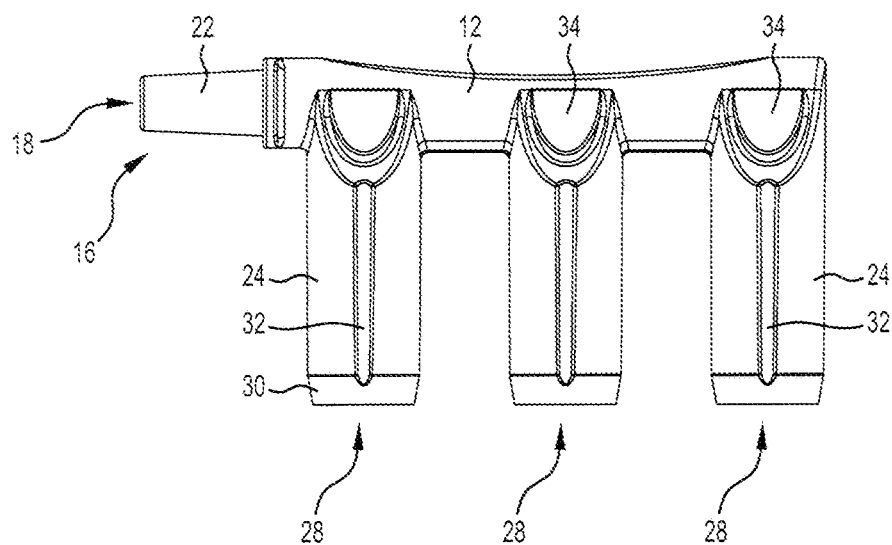
FIG. 2 shows a top view of the fluid collection device of FIG. 1.

Along the overall length of the fittings there may be a slight draft such that the outlet end has a smaller outer diameter than the end closest to the body 12. Additionally or alternatively, as shown in FIG. 2 the end of the fitting 24 may include a tapered section 30. Both of these features assist with guiding and inserting the fittings into the collection tubes. Whilst the fittings in FIG. 2 may all be a uniform size, there is an option to have a variety of different sized fittings to accommodate collection tubes of differing diameters. As will be appreciated the size of collection tubes may vary between manufacturers and may also vary depending on the volume of fluid required for particular testing purposes.

In an alternative embodiment (not shown), the fittings may have an external stepped profile that allows a single fitting to accommodate collection tubes having different diameter openings. The profile may have multiple steps.

A feature of the particular embodiment shown in the drawings is that the fluid collection device can be used as a passive fluid sampling system. This is achieved by providing an air gap when the collection tubes are connected. Although, it will be appreciated that the air gap can be omitted and vacuum tubes may be used by incorporating a piercing device into the fitting connection. Passive fluid sampling is advantageous for use with neonates, infant and children and those will fragile veins, where veins can collapse under suction pressure.

As best shown in FIGS. 1 and 2, extending along the upper surface of the fitting 24 is a depressed channel 32. The channel 32 extends from the tapered section 30 to a depression 34 at the opposing end. Further details regarding this feature will be discussed below.

Figure 5:
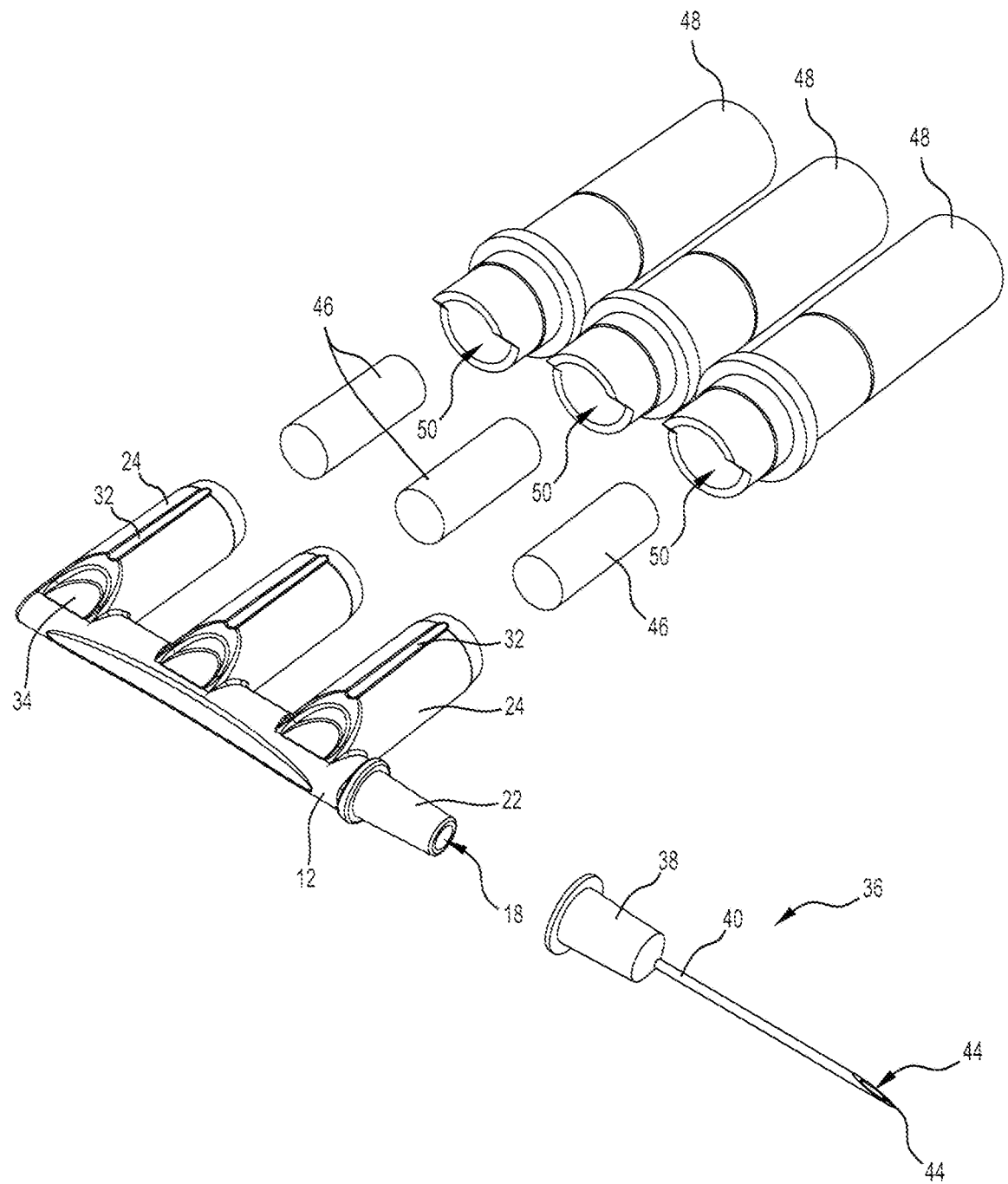
FIG. 5 shows an exploded perspective view of a fluid collection system with the fluid collection device of FIG. 1.

FIG. 5 shows an exploded view of a fluid collection system or kit. A needle 36 is provided whereby the hub 38 connects directly over connection piece 22 and a shaft 40 can be inserted into the patient by penetrating the skin with the needle point 42 and positioning part of the shaft into a patient's vein. The lumen 44 running through the shaft 40 is in fluid communication with the device inlet 18 when the hub is connected. In an alternative kit, the device 10 may be used with a butterfly needle. In this case, the needle hub is connected to one end of a flexible capillary tube. The other end of the capillary tube connects to the connection piece 22 of the device.

The connection piece 22 is slightly tapered to make connection easier and also to allow connection to different gauge needles. The most suitable needle sizes for neonates, infants and children is 21 or 23 gauge, however the device will also be suitable for larger or smaller needle gauges. The connection piece 22 may also allow for permanent connection of the needle hub to the body by bonding with adhesive. In some cases an additional seal member may be required to ensure no air can escape around the connection piece.

Collection tubes 48 can be custom made for the system, or alternatively the device is intended to suit existing standard sized collection tubes. In some embodiments, the collection tube has a collection capacity in the range of 0.3 mL to 20 mL. In paediatric applications, it may be preferable that the collection tube has a lesser volume capacity in the range of 0.3 mL to 2 mL, and more preferably a volume capacity of about 1 mL. Alternatively, in other applications the volume capacity may be e.g. 2 mL to 10 mL, and more preferably 3 mL to 5 mL. However, the volume capacity may be 10 mL to 20 mL in applications requiring larger volumes, such as veterinary applications. It will be appreciated that the volume capacity of the collection tubes may exceed the range of 0.3 mL to 20 mL, depending on the fluid sampling application, as would be understood by a person skilled in the art. The volume capacity of the tube may be increased or decreased as required by selecting a volume capacity suitable for the particular fluid sampling requirements. The device according to the invention may be produced in a variety of sizes to accommodate different applications. It will be appreciated that the collection tubes 48 are transparent so that the fluid entering the tubes is visible to the user.

Figure 6:
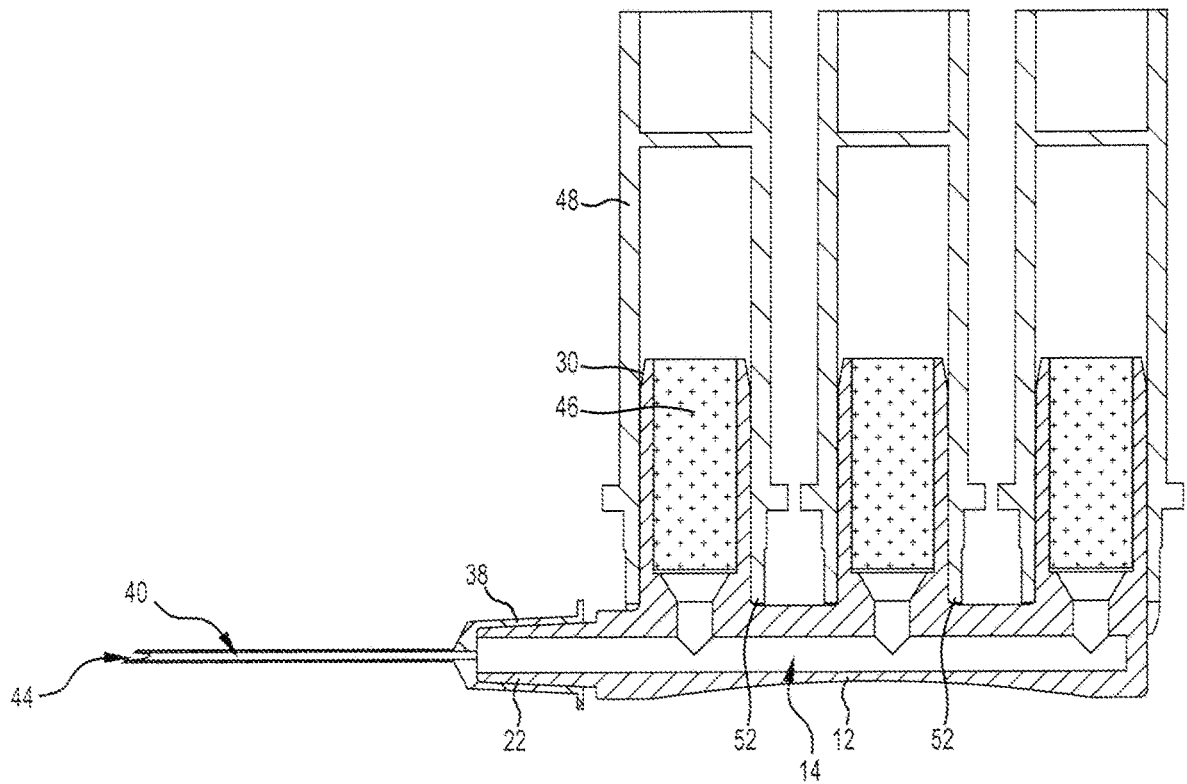
FIG. 6 shows a top cross-section view of the fluid collection system of FIG. 5 assembled.

The collection tubes 48 illustrated are generally tubular with one closed end and define an opening 50. The outside diameter of the fittings 24 are sized to fit within the openings 50 (as shown in FIG. 6). In the embodiment illustrated, the fittings 24 are inserted until the edge 52 of the openings abut the outside of the body 12, such that the collection tubes are securely fastened to the device 10. However, for an embodiment where the outside of the fitting is stepped, the collection tubes will abut a suitably sized step depending on the diameter of the tube's opening.

The collection tubes 48 are slid onto the fittings 24 to releasably engage through an interference fit. The press-fit engagement means that the collection tubes are not easily removed in use. However, once all the tubes are filled they can successively be removed by positioning the tube in an upright orientation to prevent leakage of fluid and pulled downwardly to disengage from the fitting. It will be appreciated that alternative releasable connection arrangements may be utilised, which will be readily apparent to one skilled in the art, for example a threaded engagement.

Inserted into the fittings 24 are filters 46 that allow the fluid to flow into the collection tube. The filters illustrated are made from cellulose, however a person skilled in the art will appreciate that different filter arrangements may be used. It will also be appreciated that the system will function without filters.

Figure 7:
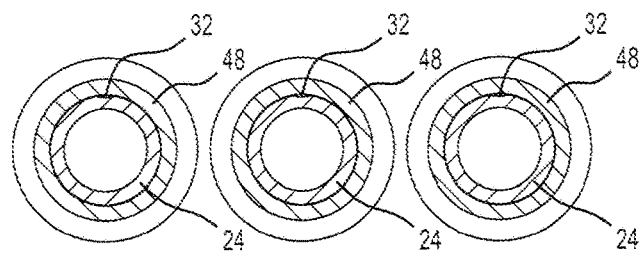
FIG. 7 shows a cross-sectional end view through the system of FIG. 6.

As mentioned above, the device is preferably configured for passive fluid collection. Whilst vacuum tubes may be utilised with a modified version of the device, the embodiment illustrated is intended for passive collection. To enable this, the depressed channels 32 run along the exterior length of the fittings 24. When a collection tube 48 is coupled to the fitting, the opening 50 is not entirely occluded, such that an air gap is created. The interior of the collection tubes are therefore in fluid communication with the ambient environment. This allows the fluid to flow directly from the vein into the needle, through the body and into the plurality of collection tubes under the veinous pressure of the subject's circulatory system. The channel 32 provides a route for air to escape from the interior of the collection tube as the fluid fills the collection tube. This air gap is illustrated in FIG. 7.

The plurality of fittings allows multiple collection tubes to be filled simultaneously or successively, depending on the location of the collection tube fittings along the body in relation to the inlet. All of the collection tubes may be filled without moving the fluid collection device and coupled collection tubes, therefore minimising pressure on the insertion site. A subject's arm can also be held in an immobilising splint device to ensure movement is minimised during sampling.

The device results in faster filling times, as time is not lost when one tube is removed and a subsequent one connected.

The multiple filling of collection tubes provides a very effective system for minimising discomfort to the subject by reducing handling of the system and the time taken to fill collection tubes. This feature combined with passive collection creates a system optimised for use with neonates, infants and children, and those with fragile veins.

Figure 8:
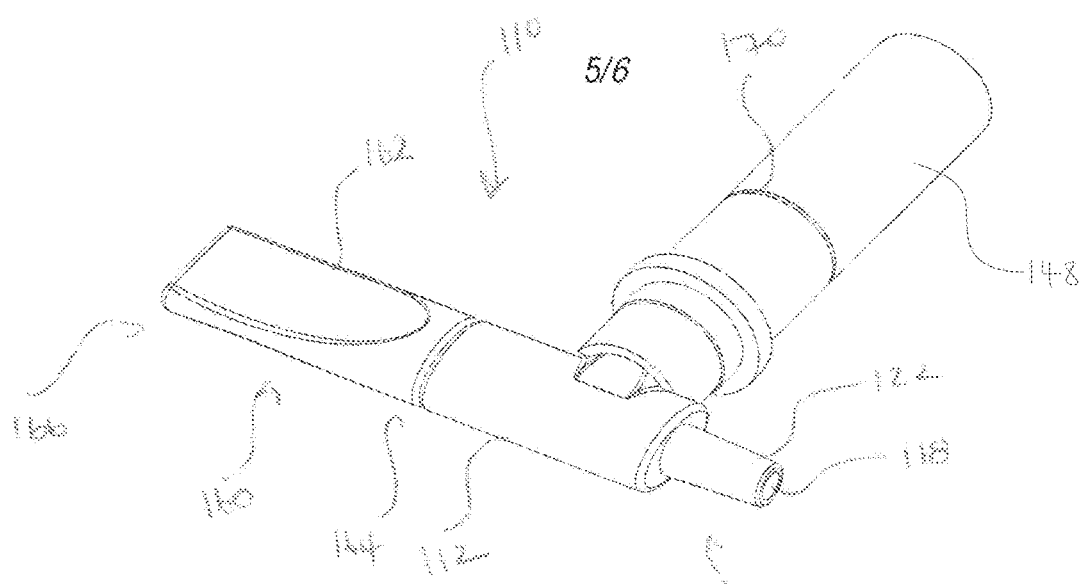
FIG. 8 shows a front perspective view of a fluid collection device according to a third embodiment.

FIG. 8 shows a fluid collection device 110 according to an alternative embodiment of the invention. In this embodiment, the fluid collection device 110 includes similar features to the fluid collection device 10 illustrated in FIGS. 1 to 7, but for the additional features described below. For example, the fluid collection device 110 includes an elongate body 112 with an internal axial bore 114 (FIG. 11), a fluid inlet 118 at a first end 116 of the body 112, and a connection piece 122 configured to connect directly to a needle hub (not shown) or indirectly to a needle hub via a flexible capillary tube (not shown).

Figure 9:
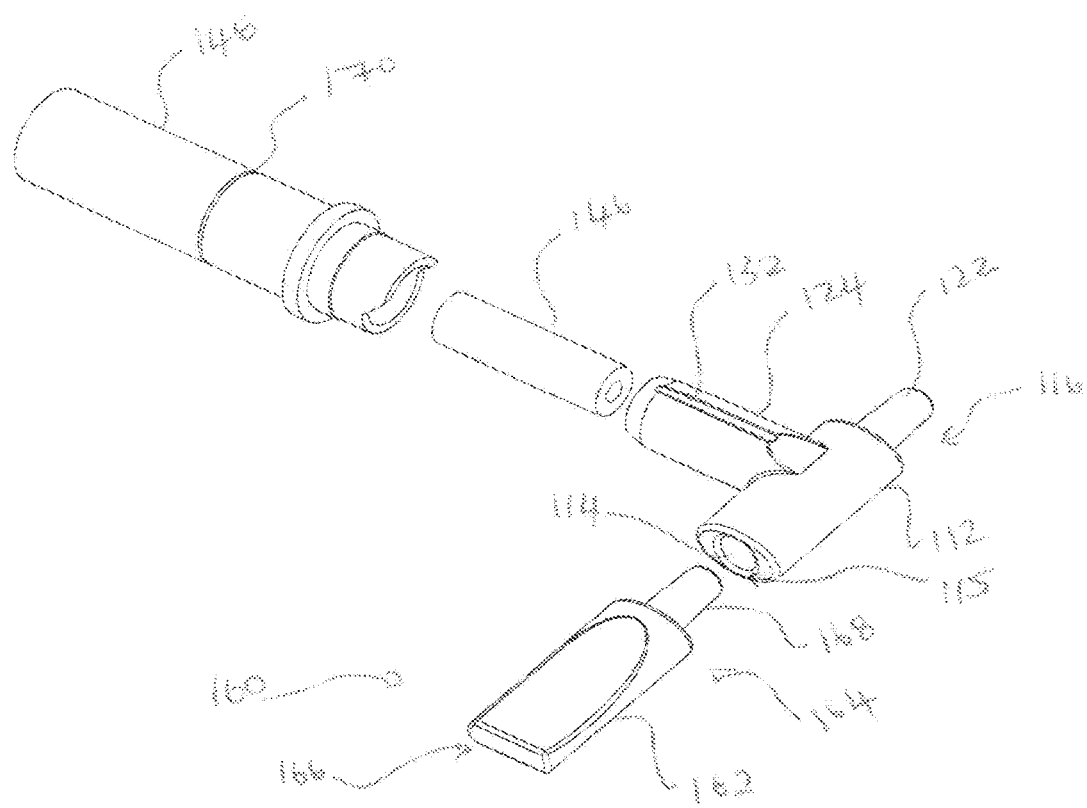
FIG. 9 shows an exploded perspective view of the fluid collection device of FIG. 8.

Unlike the fluid collection device 10 however, the fluid collection device 110 includes a single fitting 124 (FIG. 9). The fitting 124 is integral to the body 112 and projects from a side of the body 112 perpendicular to the longitudinal direction that the body 112 extends in. Similar to the fitting 24 of the fluid collection device 10, the fitting 124 is a generally tubular section having a bore with an outlet 128, and a depressed channel 132 (FIG. 9) extending along a portion of the upper surface of the fitting 124. In the same manner described above in relation to the fluid collection device 10, the fitting 124 is configured to directly releasably couple to a collection tube 148 such that fluid collected by the needle flows through the inlet 118, through the body 112 and into the fitting 124 to fill the collection tube 148. The collection tube 148 is the same as the collection tubes 48 described in respect of the fluid collection device 10. Like fluid collection device 10, the channel 132 provides a route for air to escape from the interior of the collection tube 148 as fluid fills the collection tube.

Similar to the fluid collection device 10, a filter 146 is inserted into the fitting 124 and is configured to prevent back-flow of fluid once collected in the collection tube 148. The filter 146 includes a cylindrical body with an axial bore, and is made from cellulose. However a person skilled in the art will appreciate that different filter arrangements may be used. It will also be appreciated that the system will function without the filter 146. Advantageously, the filter 146 may be adjustably positioned by a user with respect to the collection tube 148 so as to provide targeted filling of the collection tube, i.e. filling of a certain volume of fluid in the collection tube. For example, in some applications, such as when filling a coagulation tube, an exact volume of fluid is required to be collected, and the coagulation tube cannot be over-filled or under-filled. To achieve this targeted filling, the filter 146 is adjustably positioned within the fitting 124 so that a distal end thereof aligns with a volume indicator, such as indicator 170 (FIG. 8), on an exterior surface of the collection tube 148. It will be appreciated that the collection tube 148 is transparent, which would therefore allow the user to accurately align the filter 146 with respect to the volume indicator 170. The filters 46 used in the fluid collection device 10 may also be adjustably positioned with respective to the collection tubes 48 to provide targeted filling of the collection tubes 48.

The fluid collection device 110 also includes an end plug 160 that is removably connected within the bore 114 at a second end 120 of the body 112. The end plug 160 comprises a plug body 162 that is generally elliptical in side cross-section at a first end 164 thereof, and transitions into having generally rectangular side cross-section at a second, opposite, end 166. This shape enables easy finger gripping by a user. The end plug 160 also includes a connection piece 168 projecting from the first end 164 of the plug body 162. The connection piece 168 comprises a conical section which expands in diameter from its distal end toward the first end 164 of the plug body 162. The connection piece 168 is similar in form to the connection piece 122 projecting from the body 112, but does not include a bore extending therethrough. The end plug 162 is configured to plug the bore 114 at the second end 120 of the body 112 such that no fluid escapes from the fluid collection device 110 through the bore 114.

Advantageously, the end plug 160 is removable from the fluid collection device 110. This allows a second fluid collection device 210 (FIG. 10) to be connected to the first fluid connection device 110 creating a fluid connection system. To this end, the second fluid connection device is inserted within an opening 115 (FIG. 9) created by the removal of the end plug 160 from within the axial bore 114 of the fluid collection device 110. In this arrangement, fluid sampled by the needle (not shown) connected to the connection piece 122 may also flow through the body 112 of the fluid collection device 110 into the second fluid collection device 210 to be collected by a collection tube 248 coupled thereto. The collection tubes 148, 248 respectively coupled to the fluid collection devices 110, 210 may be simultaneously or successively filled with fluid sampled from the needle.

Figure 10:
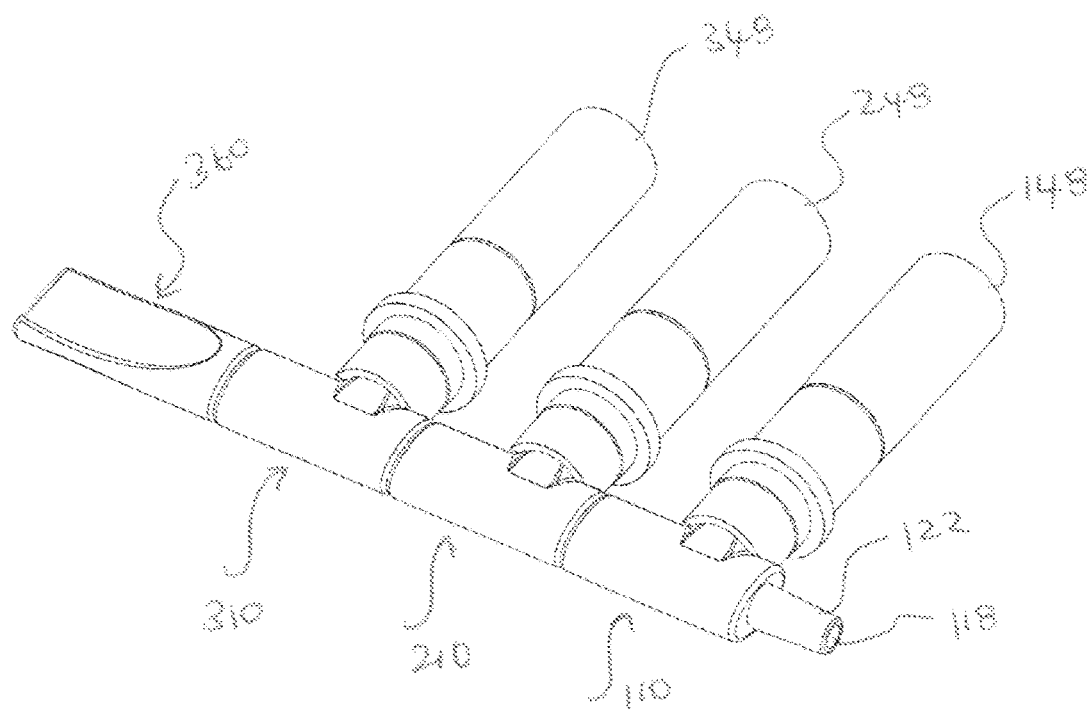
FIG. 10 shows a front perspective view of a fluid collection system comprising a plurality of the fluid collection devices of FIG. 8.
Figure 11:
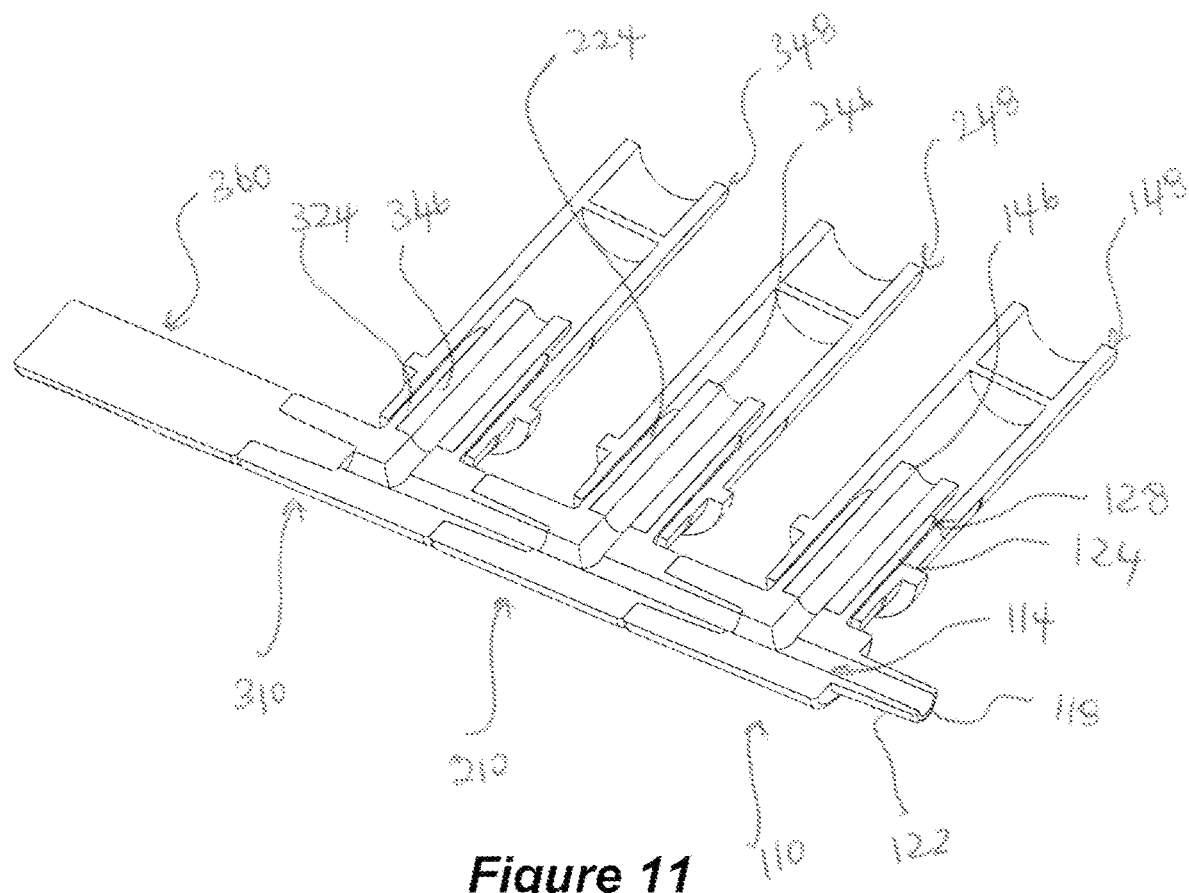
FIG. 11 shows a sectional view of the system of FIG. 10 from the same perspective as that of FIG. 10.

In the embodiment illustrated in FIGS. 10 and 11, three separate fluid collection devices 110, 210, and 310 have been releasably coupled together, in series. Fluid sampled by the needle (not shown) connected to the connection piece 122 may be collected by collection tubes 148, 248, and 348 respectively coupled to the fluid collection devices 110, 210, and 310. It will be appreciated that the distal most fluid collection device from the needle/connection piece 122, i.e. the fluid collection device 310, includes an end plug 360 such that no fluid escapes from the fluid collection device 310 during collection (or from the fluid collection system comprising the assembly of the fluid collection devices 110, 210, and 310). It will also be appreciated that the end plugs 160 and 260 have been removed from the respective fluid collection devices 110 and 260, so as to allow the three separate fluid collection devices 110, 210, and 310 to be releasably coupled together in series.

In non-illustrated embodiments, the body 12/112 may include a transparent portion shaped to form a lens that magnifies viewing of fluid flash-back into the body. The lens (not shown) is preferably located on an upper surface of the body 12/112 near the proximal end of the connection piece 22/122.

Internal surfaces of the body 12/112 may be configured to provide efficient movement of fluid therealong by, for example, having a low coefficient of friction. In one form, the internal surfaces of the body 12/112 may be coated or otherwise treated with silicone to achieve the low coefficient of friction. Alternatively or additionally, the internal surfaces may be grooved in a manner that allows for relatively faster flow of fluid therealong when compared to non-grooved surfaces.

The assembly (or system) of fluid collection devices 110, 210, 310 illustrated in FIGS. 10 and 11 has the same advantages described above in relation the fluid collection device 10. Namely, faster filling times (as time is not lost when one tube is removed and a subsequent tube is reconnected), and minimising discomfort to the subject by reducing handling of the system and the time taken to fill collection tubes. The fluid collection devices 110, 210, and 310 have the additional advantage of being releasably coupled together as desired to meet the desired sampling requirements. For example, if a relatively smaller volume of blood is required to be sampled from the subject, a single fluid collection device 110 could be utilised. On the other hand, if a relatively larger volume of blood is required to be sampled from the subject, a plurality of the fluid collection devices 110, 210, 310 could be coupled together and utilised. The fluid collection devices described above and illustrated in FIGS. 8 to 11 are therefore, advantageously, modular in design.

It will be understood that the invention disclosed and defined in this specification extends to all alternative combinations of two or more of the individual features or evident from the text or drawings. All of these different combinations constitute various alternative aspects of the invention.

The invention claimed is:
1. A fluid collection system, including:
    at least two fluid collection devices, comprising a first fluid collection device and a second fluid collection device,
    wherein the first fluid collection device and the second fluid collection device each includes:
        a body having an axial bore with a fluid inlet at one end of the axial bore and an opening at the other end of the axial bore, the fluid inlet configured to connect directly or indirectly to a needle adapted to penetrate a subject to sample fluid; and
        one or more integrally formed fittings projecting from the body, the fittings each having an outlet in fluid communication with the inlet;

each fitting configured to directly releasably couple to a collection tube such that fluid collected by the needle flows through the inlet, through the body and into the fitting to fill the coupled collection tube(s) with fluid; and wherein the first fluid collection device further includes an end plug removably connected within the opening, wherein the end plug is removable from the opening so as to allow the second fluid collection device to be releasably connected, wherein the fluid collected by the needle may also flow through the body of the first fluid collection device into the connected second fluid collection device; and wherein the first fluid collection device and the second fluid collection device are releasably coupled together by removing the end plug from at least the first fluid collection device and connecting the fluid inlet of the second fluid collection device to the opening created by the removal of the end plug from the first fluid collection device.

2. The fluid collection system of claim 1, wherein at least the first fluid collection device and the second fluid collection device of the at least two fluid collection devices are releasably coupled together, and wherein the distal most fluid collection device from the needle includes the end plug connected thereto, such that no fluid escapes from the fluid collection system during collection.

3. The fluid collection system of claim 1, wherein the first fluid collection device and the second fluid collection device configured for passive fluid collection, whereby the collection tubes are in fluid communication with the ambient environment to permit fluid to be passively collected into the collection tubes by forcing air out through an air gap.

4. The fluid collection system of claim 1, wherein the first fluid collection device and the second fluid collection device each further includes a body positioned within each of the fittings, wherein said bodies are configured to prevent backflow of fluid once the fluid is collected in the respective collection tube.

5. The fluid collection system of claim 4, wherein said bodies are adjustably positioned with respect to a respective collection tube such that an exact volume of fluid is collected by the respective collection tube.

6. The fluid collection system of claim 1, wherein the collection tubes are directly coupled to a respective fitting by being located about the respective fitting, and wherein the collection tubes are releasably coupled to a respective fitting by a frictional engagement between the collection tube and the fitting.

7. The fluid collection system of claim 1, wherein the fluid inlet of the first fluid collection device and the fluid inlet of the second fluid collection device are each tapered such that a flexibly capillary tube connected to the needle could by pushed onto a distal end of the fluid inlet until frictionally engaged thereto.

8. The fluid collection system of claim 1, wherein the first fluid collection device and the second fluid collection device are transparent or semi-transparent to allow for the tracking of fluid through the first fluid collection device and the second fluid collection device.

9. The fluid collection system of claim 1, wherein a fitting of the one or more fittings of the first fluid collection device projects from a side of the body of the first fluid collection device such that adjacent fittings of the one or more fittings of the first fluid collection device are perpendicular to a longitudinal direction in which the body of the first fluid collection device extends; and wherein a fitting of the one or more fittings of the second fluid collection device projects from a side of the body of the second fluid collection device such that adjacent fittings of the one or more fittings of the second fluid collection device are perpendicular to a longitudinal direction in which the body of the second fluid collection device extends.

10. The fluid collection system of claim 1, wherein the end plug of the first fluid collection device is configured to prevent loss of fluid from the first fluid collection device through the bore.

11. The fluid collection system of claim 1, wherein the second fluid collection device is of the same construction as the first fluid collection device.

12. A kit, including:
a fluid collection device, including:
a body having an axial bore with a fluid inlet at one end of the axial bore and an opening at the other end of the axial bore, the fluid inlet configured to connect directly or indirectly to a needle adapted to penetrate a subject to sample fluid; and
one or more integrally formed fittings projecting from the body, the fittings each having an outlet in fluid communication with the inlet;
each fitting configured to directly releasably couple to a collection tube such that fluid collected by the needle flows through the inlet, through the body and into the fitting to fill the coupled collection tube(s) with fluid; and
an end plug removably connected within the opening, wherein the end plug is removable from the opening so as to allow a second fluid collection device to be releasably connected, wherein the fluid collected by the needle may also flow through the body into the connected second fluid collection device;
wherein the kit further includes:
a needle adapted to penetrate a subject to sample fluid, the fluid inlet of the fluid collection device configured to connect directly or indirectly to the needle; and
a collection tube, whereby the fitting is configured to directly releasably couple to a collection tube such that fluid collected by the needle flows through the inlet, through the body and into the fitting to fill the coupled collection tube with fluid.

13. The kit of claim 12, wherein the fluid collection device is a first fluid collection device, and the second fluid collection device is of the same construction as the first fluid collection device, and wherein the kit further includes a plurality of each of the first fluid collection device and the second fluid collection device and a plurality of collection tubes.

14. The kit of claim 12, wherein the kit includes a plurality of collection tubes having different volume capacities.

* * * * *